Aug. 13, 1974 L. H. SHOESMITH Plant Pat. 3,588
CHRYSANTHEMUM PLANT
Filed Aug. 10, 1972
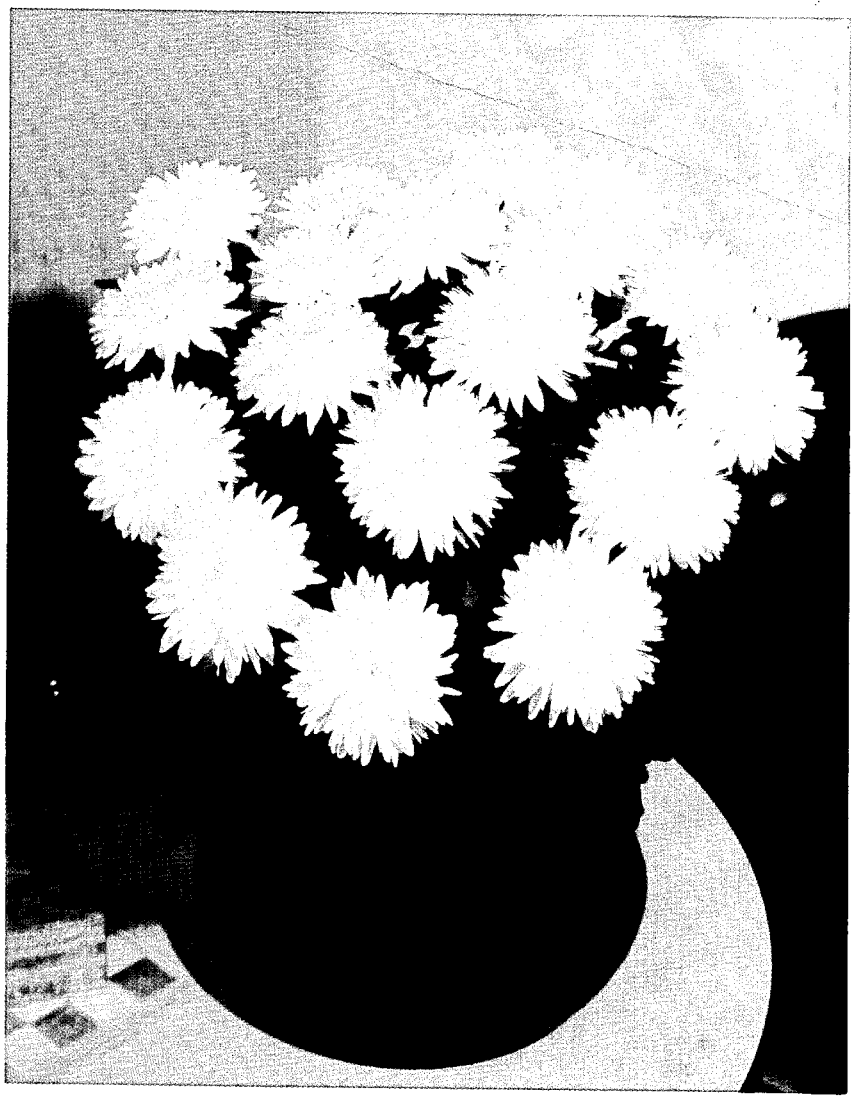
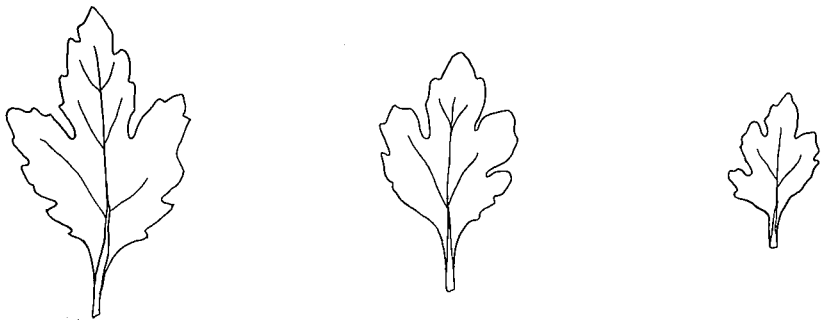

United States Patent Office

Plant Pat. 3,588
Patented Aug. 13, 1974

3,588

CHRYSANTHEMUM PLANT

Leonard H. Shoesmith, Westfield-Woking, England, assignor to Pan-American Plant Company, Chicago, Ill.

Filed Aug. 10, 1972, Ser. No. 279,512
Int. Cl. A01h *5/00*
U.S. Cl. Plt.—78 1 Claim

ABSTRACT OF THE DISCLOSURE

A new variety of chrysanthemum plant particularly suited for summertime greenhouse production as a pot plant and having a dependable nine-week response for photoperiod culture. This is a vigorous variety producing a strong, well branched plant when grown as a pot mum and appears to have no tendency to heat delay in warm seasons. In the wintertime, the flowers of this variety develop a light bronze coloring as they open but as the seasons become warmer, the flower color is a good and attractive yellow.

BACKGROUND OF THE NEW PLANT

This new chrysanthemum variety was developed as a seedling of unknown parentage resulting from random crossing of greenhouse plants during the course of an extensive breeding program carried on by me and under my direction with the object of producing new and distinctive chrysanthemum varieties having improved characteristics of growth, response, and flower form and color. This plant was discovered by me in November 1968 at West Chicago, Ill., and asexual propagation, at West Chicago, Ill. by means of cuttings from the original plant, having demonstrated this variety to have good characteristics for summertime flowering, resulted in this plant being selected for trials which proved the plant to have commercial value. Extensive propagation of this new variety by means of vegetative cuttings, at West Chicago, Ill., and at Cortez, Fla., has shown the distinctive features of the plant to hold true from generation to generation and to be firmly fixed.

DESCRIPTION OF THE DRAWING

This new variety of chrysanthemum plant is illustrated by the accompanying drawings which show the color and form of the flower as nearly true as is reasonably possible by conventional photographic procedures, and which show the configuration of typical specimens of the leaves by pen-in-ink sketches.

DESCRIPTION OF THE NEW PLANT

The following is a detailed description of my new variety of chrysanthemum plant with color designations according to the Horticultural Colour Chart issued by The British Colour Council in collaboration with the Royal Horticultural Society.

*The plant*

Origin: Seedling.
Parentage: Unknown, this seedling resulting from random crosses of greenhouse plants.
Classification:
*Botanic.*—*Chrysanthemum morifolium.*
*Commercial.*—Greenhouse pot plant.
Form: Perennial herbaceous bush.
Height: 10 inches.
Growth: Terminal. Vigorous and upright with good characteristics of sturdiness and strength.
Branching: Much branching when terminal bud is removed.
Foliage: Abundant. 12 leaves per 6 inches of stem.

*Leaf size.*—Mature leaf—About 4¼ inches long by 2½ inches wide.
*Shape.*—Lanceolate and lobed with margins very slightly serrated.
*Surface texture.*—Glaucous.
*Color.*—Upper side—Spinach Green 0960. Under side—Spinach Green 0960/2.
*Venation.*—Nearly palmately veined.
*Petioles.*—Absent—leaf is sessile.

*The bud*

Form: Globular.
Size: ¾ inch in diameter when phyllaries are just breaking open.
Opening rate: Bud opens slowly.
Color:
*When phyllaries first divide.*—Indian Yellow 6/2.
*When florets begin to unfurl.*—Yellow Ochre 07.
Phyllaries: The outside of the receptacle bears many involucral bracts or phyllaries that are distinct. These bracts are spear shaped and stand up.
*Color.*—Inside—Scheeles Green 860/1. Outside—Scheeles Green 860.
*Surface aspect.*—Canescent.
Calyx: The calyx is represented by tiny bristles arising from the top of the ovary and in some cases it may be absent.
Peduncle: Length—1 to 1½ inches.
*Surface aspect.*—Canescent.
*Strength.*—Erect with small modified leaf attached to each peduncle.

*The flower*

Response: Dependable 9 week.
Recommended flowering: March through November.
Natural season flowering: Late October.
Blooms: Flower type—decorative.
*Borne.*—A head of many florets borne on a receptacle.
*Size.*—Medium, 3½ to 4 inches in diameter and about 1 inch in depth.
*Shape.*—Flat-ray type.
*Florets*: Numerous ray florets. Form: Linear with obtuse apex, 1½ to 2 inches long. Color: Outer floret—Canary Yellow 2, with base of Pod Green 061. Inside floret—Sulphur Yellow 1/1. Reverse side of florets—Sulphur Yellow 1/2. Firmness: Soft. Appearance: Velvety. Discoloration: None.
*Peduncle.*—1 to 1½ inches long, sturdy and upright.
Color: Spinach Green 0960.
Persistence: Florets hang on and dry.
Effect of Weather: Plant is not affected by wet or hot weather. In wintertime flowering, a light bronze coloring develops as the flower opens. As seasons become warmer, the color becomes a good consistent yellow.
Lasting quality: On the plant, the blooms are long lasting. These blooms are not used as cut flowers.

*Reproductive organs*

Stamens: This plant does not appear to possess stamens and there is no pollen.
Pistils: Number—one for each ray floret.
*Styles.*—Length—¼ inch.
*Stigmas.*—Color—Straw Yellow 604.

This new variety of chrysanthemum plant most nearly resembles the variety Yellow Mandalay (unpatented). This variety is more vigorous than Yellow Mandalay and trials have shown it to be better suited for summertime flowering since it does not have any tendency to heat delay as does Yellow Mandalay.

The flowering response of this new variety is nine weeks consistently, this plant flowering about four days earlier than Yellow Mandalay. In wintertime, this variety develops a light bronze coloring as the flower opens. The flower color becomes a good yellow, however, as the seasons become warmer.

I claim:

1. A new and distinct variety of chrysanthemum plant, substantially as herein shown and described, characterized by its dependable nine-week response and vigorous growth, its lack of tendency to heat delay during summertime flowering, and its capability of producing a strong well branched plant when grown as a pot plant.

No references cited.

ROBERT E. BAGWILL, Primary Examiner